US009668803B2

(12) United States Patent
Bhushan et al.

(10) Patent No.: US 9,668,803 B2
(45) Date of Patent: *Jun. 6, 2017

(54) IMPEDANCE COMPUTATION FOR ABLATION THERAPY

(71) Applicant: Medtronic, Inc, Minneapolis, MN (US)

(72) Inventors: Nikhil Bhushan, Plymouth, MN (US); Thomas R. Skwarek, Shoreview, MN (US); Graham Spall, Plymouth, MN (US); Keith S. Bosacker, St. Anthony, MN (US)

(73) Assignee: Medtronic, Inc., Minneapolis, MN (US)

(*) Notice: Subject to any disclaimer, the term of this patent is extended or adjusted under 35 U.S.C. 154(b) by 117 days.

This patent is subject to a terminal disclaimer.

(21) Appl. No.: 14/454,315

(22) Filed: Aug. 7, 2014

(65) Prior Publication Data
US 2014/0350543 A1    Nov. 27, 2014

Related U.S. Application Data

(63) Continuation of application No. 13/022,015, filed on Feb. 7, 2011, now Pat. No. 8,801,704, which is a (Continued)

(51) Int. Cl.
*A61B 18/12* (2006.01)
*A61B 18/16* (2006.01)
(Continued)

(52) U.S. Cl.
CPC ...... *A61B 18/1233* (2013.01); *A61B 18/1206* (2013.01); *A61B 18/14* (2013.01);
(Continued)

(58) Field of Classification Search
CPC ........ A61B 18/1206; A61B 2018/1253; A61B 2018/00702; A61B 2018/00696;
(Continued)

(56) References Cited

U.S. PATENT DOCUMENTS 5,496,312 A * 3/1996 Klicek ............... A61B 18/1206
606/34
5,558,671 A    9/1996 Yates
(Continued)

FOREIGN PATENT DOCUMENTS

WO    2003008039 A1    1/2003
WO    2006045090 A2    4/2006

OTHER PUBLICATIONS

Smith, K.C.A. and R.E. Alley. Electrical Circuits. Cambridge: Cambridge University Press, 1992. pp. 66-67.*
(Continued)

*Primary Examiner* — Jaymi Della
(74) *Attorney, Agent, or Firm* — Shumaker & Sieffert, P.A.

(57) ABSTRACT

This disclosure describes impedance computation techniques that may reduce the effect of crosstalk, thus generating more accurate impedance measurements. In particular, an ablation system models the electrical interaction among the active electrodes and a common return electrode using a star-configuration resistor model. The ablation system computes one or more parameters of the star-configuration resistor model and adjusts the therapy based on at least the computed parameters of the star-configuration resistor model.

11 Claims, 8 Drawing Sheets

Related U.S. Application Data continuation of application No. 11/694,526, filed on Mar. 30, 2007, now Pat. No. 7,896,871.

(60) Provisional application No. 60/891,100, filed on Feb. 22, 2007.

(51) Int. Cl.
*A61B 18/14* (2006.01)
*A61B 18/00* (2006.01)

(52) U.S. Cl.
CPC .......... *A61B 18/16* (2013.01); *A61B 18/1477* (2013.01); *A61B 2018/00577* (2013.01); *A61B 2018/00648* (2013.01); *A61B 2018/00702* (2013.01); *A61B 2018/00827* (2013.01); *A61B 2018/00875* (2013.01); *A61B 2018/1425* (2013.01); *A61B 2018/1467* (2013.01); *A61B 2018/1472* (2013.01); *A61B 2018/162* (2013.01); *A61B 2218/002* (2013.01)

(58) Field of Classification Search
CPC .. A61B 2018/0072; A61B 2018/00767; A61B 2018/00773; A61B 2018/00827; A61B 2018/0875; A61B 2018/00892
See application file for complete search history.

(56) References Cited

U.S. PATENT DOCUMENTS

| | | |
|---|---|---|
| 5,713,896 A | 2/1998 | Nardella |
| 5,817,093 A | 10/1998 | Williamson, IV et al. |
| 6,293,941 B1 | 9/2001 | Strul et al. |
| 6,302,898 B1* | 10/2001 | Edwards .......... A61B 17/00491 606/213 |
| 6,696,844 B2 | 2/2004 | Wong et al. |
| 6,730,079 B2 | 5/2004 | Lovewell |
| 6,855,141 B2 | 2/2005 | Lovewell |
| 7,896,871 B2 | 3/2011 | Bhushan et al. |
| 8,801,704 B2 | 8/2014 | Bhushan et al. |
| 2002/0058933 A1 | 5/2002 | Christopherson et al. |
| 2003/0032989 A1* | 2/2003 | Herleikson .......... A61B 5/0531 607/8 |
| 2004/0015160 A1* | 1/2004 | Lovewell .......... A61B 18/1206 606/34 |
| 2004/0078038 A1 | 4/2004 | Desinger et al. |
| 2005/0222562 A1 | 10/2005 | Lovewell |

OTHER PUBLICATIONS

Smith et al., "Electrical Circuits," Cambridge, Cambridge University Press, 1992, 4 pp. (Applicant points out that, in accordance with MPEP 609.04(a), the 1992 year of publication is sufficiently earlier than the effective U.S. filing date and any foreign priority date of Feb. 22, 2007 so that the particular month of publication is not in issue.).

International Search Report and Written Opinion from International Application No. PCT/US2008/050129, dated Jun. 6, 2008, 13 pp.

Prosecution History from U.S. Appl. No. 11/694,526, dated Jun. 10, 2010 through Oct. 26, 2010, 48 pp.

Prosecution History from U.S. Appl. No. 13/022,015, dated Nov. 25, 2013 through Jul. 19, 2014, 34 pp.

* cited by examiner

IMPEDANCE COMPUTATION FOR ABLATION THERAPY

This application is a continuation of U.S. patent application Ser. No. 13/022,015, entitled "IMPEDANCE COMPUTATION FOR ABLATION THERAPY", filed Feb. 7, 2011, and issued as U.S. Pat. No. 8,801,704 on Aug. 12,2014, which is a continuation of U.S. patent application Ser. No. 11/694,526, entitled "IMPEDANCE COMPUTATION FOR ABLATION THERAPY," filed Mar. 30, 2007 and issued as U.S. Pat. No. 7,896,871 on Mar. 1, 2011, which claims the benefit of U.S. Provisional Application No. 60/891,100, filed Feb. 22, 2007. The entire content of each of application Ser. Nos. 13/022,015, 11/694,526, and 60/891,100 is incorporated herein by reference.

TECHNICAL FIELD

The invention relates to medical devices and, more particularly, to monitoring electrical impedances within a therapy delivery device.

BACKGROUND

Ablation therapy is a surgical technique used to destroy or selectively remove tissue to reduce or eliminate patient conditions. Many different technologies are directed to tissue ablation. Such technologies include electrical ablation, ultrasound ablation, microwave ablation, cryoablation, conductive heating, radioactive heating, and combination ablation that includes more than one technology. Electrical ablation utilizes electrical current to heat the target tissue, and may include techniques such as radio frequency (RF) ablation and other electrical ablation technologies.

One example of an ablation therapy is treatment for benign prostatic hyperplasia (BPH). BPH is a condition caused by the second period of continued prostate gland growth. This growth begins after a man is approximately 25 years old and may begin to cause health problems after 40 years of age. The prostate growth eventually begins to constrict the urethra and may cause problems with urination and bladder functionality. Ablation therapy attempts to create a lesion in the prostate and decrease the prostate size, restoring appropriate bladder function.

SUMMARY

In general, this disclosure describes techniques for modeling an electrical interaction among active electrodes that delivery energy to tissue of a patient and a common return electrode using a star-configuration resistor model. The star-configuration resistor model is a model in which one terminal of each of the resistors is coupled at a central node. Processor may monitor and/or control a therapy being delivered to the patient based on one or more parameters of the star-configuration model. As an example, processor may adjust one or more parameters of the therapy based on impedances of the star-configuration model computed using a series of energy bursts.

In one embodiment, a method for delivering therapy to a patient comprises modeling an electrical interaction between a first and second active electrode that deliver energy to a target tissue location of a patient and a return electrode using a star-configuration resistor model in which all of the resistors are coupled to each other at a common node, applying energy to one or more different combinations of the first and second active electrodes to compute one or more parameters of the star-configuration resistor model, delivering a therapy to the patient, and adjusting one or more parameters of the therapy based on at least one of the computed parameters of the star-configuration resistor model.

In another embodiment, a therapy delivery device comprises a first active electrode that delivers energy to a target tissue location of a patient, a second active electrode that delivers energy to the target tissue location of the patient, a return electrode that operates as a destination for the energy delivered via the first and second active electrodes, a generator that delivers therapy energy to the patient via the first and second active electrodes, and a processor that models an electrical interaction between the first and second active electrode and the return electrode using a star-configuration resistor model in which all of the resistors are coupled to each other at a common node. The processor causes the generator to apply energy to one or more different combinations of the first and second active electrodes, computes one or more parameters of the star-configuration resistor model based on measurements made during application of energy to the different combinations of the active electrodes, and adjusts one or more parameters of the therapy based on at least one of the computed parameters of the star-configuration resistor model.

In a further embodiment, a computer-readable medium comprises instructions that cause a processor to model an electrical interaction between a first and second active electrode that deliver energy to a target tissue location of a patient and a return electrode using a star-configuration resistor model in which all of the resistors are coupled to each other at a common node, apply energy to one or more different combinations of the first and second active electrodes to compute one or more parameters of the star-configuration resistor model, deliver a therapy to the patient, and adjust one or more parameters of the therapy based on at least one of the computed parameters of the star-configuration resistor model.

The details of one or more embodiments of this disclosure are set forth in the accompanying drawings and the description below. Other features, objects, and advantages of this disclosure will be apparent from the description and drawings, and from the claims.

DETAILED DESCRIPTION

This disclosure describes techniques for reducing the effects of crosstalk in electrical impedance measurements in a multi-electrode ablation system. During electrical ablation, such as radio frequency (RF) ablation, an ablation system delivers energy to two or more electrodes in contact with or in close proximity to a target tissue location within the body of a patient. The energy passes from the electrodes of the ablation system to the target tissue location, causing heating of the tissue. The ablation system continues to deliver energy to the tissue location via the electrodes until the tissue location is heated to a high enough temperature to cause ablation of the tissue. The ablation system may deliver the energy to the tissue location via both electrodes simultaneously for a particular duration of time.

The amount of energy delivered to the target tissue location may be adjusted to control the ablation therapy. In some embodiments, the amount of energy delivered to each of the respective electrodes may be independently controlled. To assist in controlling the energy delivery of the ablation system, the impedance levels between each of the electrodes to which energy is delivered and a common return electrode may be monitored. One or more parameters of the therapy may be controlled based on the respective impedance measurements. In this manner, the ablation system may be configured to operate within specific impedance limits to avoid damage to the target tissue location. In some ablation systems, the electrodes are located in close proximity of each other. This may result in crosstalk between the two or more electrodes, which may affect the impedance measurements between each of the electrodes to which energy is delivered and the common return electrode. In some cases, crosstalk can result in erroneously high impedance measurements that result in erroneous reductions in the amount of energy delivered to the electrode.

The impedance measurement techniques described herein model the electrical interaction among the active electrodes and a common return electrode using a star-configuration resistor model. The star-configuration resistor model is a model in which one terminal of each of the resistors is coupled at a central node. In fact, the resistors are only interconnected via this central node. The ablation system computes one or more parameters of the star-configuration resistor model and adjusts the therapy based on at least the computed parameters of the star-configuration resistor model. The parameters of the star-configuration model may be, for example, one or more impedances along the different legs of the star-configuration resistor model, impedances between each of the active electrodes and the common return electrode, voltages measured during a series of pulses, currents measured during the series of pulses or the like. In one embodiment, the ablation system may use the values of the parameters of the star-configuration model to compute adjusted impedance values that remove the crosstalk between the electrodes. Moreover, the ablation system may compute these more accurate impedance measurements without requiring deactivation of one of the active electrodes during the ablation therapy.

Figure 1:
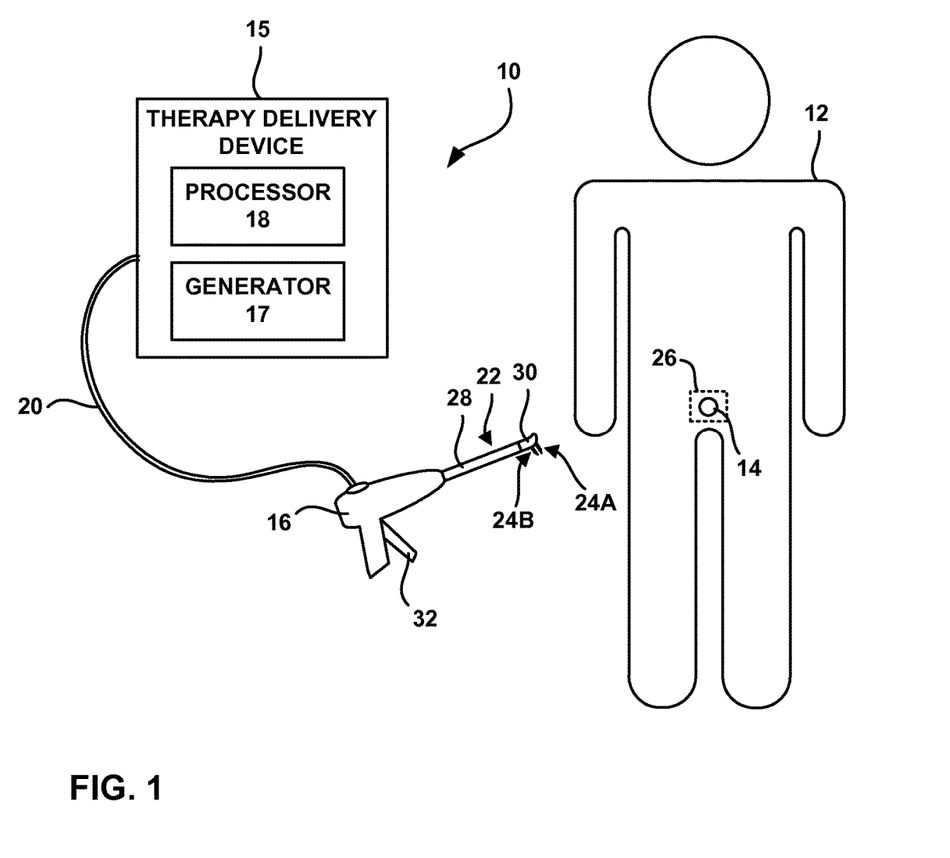
FIG. 1 is a conceptual diagram illustrating an example ablation system in conjunction with a patient.

FIG. 1 is a conceptual diagram illustrating an example ablation system 10 in conjunction with a patient 12. Ablation system 10 delivers therapy to treat a condition of patient 12. In particular, ablation system 10 provides energy, such as RF energy, to a target tissue location 14 of patient 12 to heat the tissue in order to ablate at least a portion of target tissue location 14. In the example illustrated in FIG. 1, target tissue location 14 is tissue of the prostate gland. Ablation of prostate tissue may destroy a portion of the enlarged prostate caused by, for example, benign prostatic hyperplasia (BPH). Ablation system 10 may also be used on target tissue locations other than the prostate. For example, ablation system 10 may provide ablation therapy to cardiac tissue, ovarian cysts, colon polyps, tumors, or any other internal or external tissue of patient 12.

Ablation system 10 includes a therapy delivery device 15 coupled to an ablation device 16. Therapy delivery device 15 includes a generator 17 that generates energy to provide to target tissue location 14 for ablation therapy. To this end, generator 17 may include circuitry for developing RF energy from a direct current (DC) power source, such as a rechargeable battery, or drawn from an alternating current (AC) power source, such as an electrical outlet. Generator 17 may generate the energy within defined therapy parameters to provide appropriate heating of target tissue location 14. In some embodiments, generator 17 may be a different type of energy source. For example, generator 17 may convert power from a power source to produce steam, mechanical energy, or any other type of output that may perform ablation on patient 12. Other energy may be laser energy or ultrasound energy. In this manner, generator 17 may produce electrical, chemical, or mechanical energy.

Therapy delivery device 15 also includes a processor 18 that controls generator 17 to deliver energy according to therapy parameters. The therapy parameters may include an amount of time the therapy is applied, voltage levels of the therapy and the like. As will be described in more detail below, processor 18 may compute impedance measurements during delivery of ablation therapy in accordance with the techniques described herein. Processor 18 may also control the delivery of the therapy to target tissue location 14 based on the computed impedance measurements. Alternatively, processor 18 may display the computed impedance measurements to a clinician or other user of ablation system 10. In this case, the user may control the delivery of energy to target tissue location 14 based on the computed impedance measurements. Processor 18 may comprise any one or more of a microprocessor, digital signal processor (DSP), application specific integrated circuit (ASIC), field-programmable gate array (FPGA), or other digital logic circuitry.

Therapy delivery device 15 transmits the energy through an electrical cable 20 to ablation device 16. Electrical cable 20 may include one or more conductors that electrically couple generator 17 to ablation device 16 to provide the energy to ablation device 16. Alternatively, generator 17 and ablation device 16 may be coupled via more than one electrical cable. Ablation device 16 transmits the energy through a catheter 22 and delivers the energy to target tissue location 14 via electrodes 24A and 24B (collectively, "electrodes 24"). In the example illustrated in FIG. 1, electrodes 24 comprise needle electrodes that extend from catheter 22 to penetrate target tissue location 14. However, other types of electrodes may be used in place of needle electrodes. For example, ablation device may deliver energy to target tissue location 14 via ring electrodes located on the distal end of catheter 22.

Catheter 22 includes one or more channels that house needle electrodes 24. In some embodiments, each of needle electrodes 24 is located within a separate channel. Catheter 22 may include additional channels for other features of ablation device 16, such as a channel for insertion of cystoscope or a channel for a fluid delivery tube. Thus, catheter 22 may provide a conduit for both energy from generator 17 and fluid from a pump (not shown in FIG. 1). Catheter 22 may be formed in various diameters to enter through different orifices of patient 12. Catheter 22 may be produced in different lengths with different configurations of electrodes based on the type of therapy to be delivered or the location of patient 12 to which the therapy will be delivered.

Catheter 22 includes shaft 28 and tip 30. Shaft 28 may be permanently coupled to a housing of catheter 22. Alternatively, shaft 28 may be detachable and simply locked in place for a treatment session. In this manner, shaft 28 may be replaced and discarded after a single use. Shaft 28 may couple to tip 30 by, for example, a screw mechanism, snap fit, or adhesives. Tip 30 includes one or more openings that allow the electrodes 24 to exit catheter 22 and extend into target tissue location 14. Shaft 28 may be a rigid structure that is manufactured of stainless steel or other metal alloy and insulated with a polymer such as nylon or polyurethane. Alternatively, shaft 28 may be constructed of a rigid polymer or composite material. In some applications, shaft 28 may be made of a slightly more flexible material. In some embodiments, tip 30 may be constructed of an optically clear polymer such that the clinician may view the urethra or other bodily cavity using a cystoscope during insertion of catheter 22 into patient 12. However, a transparent tip 30 is not required.

Ablation system 10 further includes a return electrode 26 that operates as a destination for the energy delivered via electrodes 24. Return electrode 26 may, for example, be a ground pad placed at an exterior location on patient 12 on or near the opposing side of target tissue location 14. In the example illustrated in FIG. 1, return electrode 26 is placed on the lower back of patient 12. Alternatively, return electrode 26 may extend from ablation device 16 to be placed within the patient. In either case, energy delivered by generator 17 travels from respective ones of electrodes 24 to return electrode 26.

In some embodiments, generator 17 may independently control the amounts of energy delivered to each of electrodes 24. Thus, generator 17 may deliver different amounts of energy to each of the electrodes 24. More specifically, generator 17 may deliver a first amount of energy to electrode 24A via a first conductor within electrical cable 20 and deliver a second amount of energy to electrode 24B via a second conductor within electrical cable 20. Alternatively, in the case in which more than one electrical cable couples generator 17 to ablation device 16, generator 17 may deliver a first amount of energy to electrode 24A via a first electrical cable and may deliver a second amount of energy to electrode 24B via a second electrical cable. In this manner, ablation system 10 operates each of electrodes 24 in an independent, monopolar fashion.

When the energy is being delivered, target tissue location 14 may increase in temperature, thus destroying a certain volume of tissue. This heating may last a few seconds or a few minutes, depending on the condition of target tissue location 14 and the desired therapy. To control and/or monitor the ablation therapy, ablation system 10 measures impedances between each of electrodes 24 and common return electrode 26. Based on the respective impedance measurements, the one or more parameters of the therapy being delivered via electrodes 24 may be adjusted. In one embodiment, processor 18 adjusts one or more parameters of the delivered therapy when one of the impedance measurements exceeds a threshold impedance. For example, processor 18 may reduce the amount of energy delivered to the one of electrodes 24 corresponding to the high impedance measurement. In this manner, ablation system 10 operates within configured impedance limits. Alternatively, processor 18 may display the computed impedance measurements to a clinician or other user of ablation system 10. In this case, the user may control the delivery of energy to target tissue location 14 based on the computed impedance measurements.

Since electrodes 24 are located in close proximity to one another when disposed in target tissue location 14, crosstalk between electrodes 24 may affect the impedance measurements. More specifically, current may travel from one of electrodes 24 down the circuit of the other one of electrodes 24 to generator 17. This crosstalk can result in erroneous impedance measurements. In some cases, the result is an erroneously high impedance measurement. The erroneously high impedance measurement may result in unwanted reductions in energy to the one of electrodes 24 corresponding with the high impedance measurement. Computing impedance measurements in accordance with the star-configuration resistor model may reduce the effect of crosstalk on the impedance measurements, thus providing more accurate impedance measurements. In particular, processor 18 models the electrical interaction among electrodes 24 and common return electrode 26 using a star-configuration resistor model, and computes the impedance measurements as a function of this model.

Processor 18 computes one or more parameters of the star-configuration model via a series of energy bursts on electrodes 24. In particular, ablation system 10 measures one or more voltages and currents during delivery of the series of energy bursts to different electrode combinations, and computes one or more impedances based on the measured voltages and currents. The measured voltages, the measured currents, and the computed impedances comprise the one or more parameters of the star-configuration resistor model. In one embodiment, processor 18 may compute a common impedance to return electrode 26. Subsequently, during the ablation therapy, processor 18 measures a number of electrical parameters of the therapy, such as impedances of electrodes 24, currents running through electrodes 24, and the like. Using the electrical parameters measured during the ablation therapy as well as one or more of the computed parameters of the star-configuration model, such as the voltages, currents or computed impedances of the model, processor 18 calculates adjusted impedances between electrodes 24 and return electrode 26. Again, the electrical parameters are those parameters measured during the therapy while the parameters of the star-configuration resistor model are either computed prior to beginning the therapy or during an interruption in the therapy.

Processor 18 may compute the impedances of the star-configuration resistor model prior to beginning delivery of the therapy to the patient. Thus, the impedance measurement techniques described herein may be performed on-the-fly without requiring periodic deactivation of electrodes 24 during the ablation therapy. Therefore, there is no disruption to the ablation therapy. Alternatively, processor 18 may compute the impedances of the star-configuration resistor model after beginning delivery of the therapy to the patient. In this case, processor 18 may interrupt delivery of the therapy to compute the impedances of the star-configuration resistor model.

In another embodiment, processor 18 may compute a common impedance at two different instances of time. For example processor 18 may compute the common impedance to return electrode 26 prior to beginning therapy and then after beginning therapy, or at two different instances in time after beginning delivery of the therapy. Processor 18 may compare the computed common impedances to return electrode 26 and adjust one or more parameters of the therapy based on the comparison. For example, if the difference between the two computed common impedances exceeds a threshold, it may be an indication that placement of the electrodes is not in an ideal location or that one of electrodes 24 is broken. Thus, the user of ablation system 10 may adjust the location of electrodes 24 or remove electrodes 24 entirely and test them outside of the patient. A similar determination may be made using parameters of the star configuration model prior to initiating therapy.

Ablation device 16 may be embodied as a hand-held device as shown in FIG. 1. Ablation device 16 may include a trigger 32 to control the start and stop of therapy. Trigger 32 may be pressure sensitive, where increased pressure of trigger 32 provides an increased amount of energy to the tissue of target tissue location 14. Trigger 32 may also be used to deploy electrodes 24 into target tissue location 14.

In some cases, ablation device 16 may only be used for one therapy session. Reuse may cause infection and contamination, so it may be desirable for ablation device 16 to only be used once per patient. Alternatively, ablation device 16 may be used more than once, but catheter 22 may be discarded after each use, and replaced with a new catheter for the next therapy session.

Although the techniques of this disclosure are described in terms of "dry" ablation therapy, the techniques are equally applicable in an ablation system 10 that delivers a conductive fluid to interact with the energy being delivered by electrodes 24, often referred to as "wet" ablation. Delivering a conductive fluid for wet ablation may increase the effective heating area of electrodes 24, thus increasing therapy efficacy. In a wet ablation system, therapy delivery device 15 may include a pump (not shown in FIG. 1) to pump fluid through a tube (not shown in FIG. 1) into ablation device 16. The fluid is then delivered through catheter 22 to target tissue location 14. In some embodiments, the conductive fluid may exit small holes in needle electrodes 24 and flow around electrodes 24. The conductive fluid, e.g., saline, may increase the effective heating area and decrease the heating time for effective treatment.

Figure 2A:
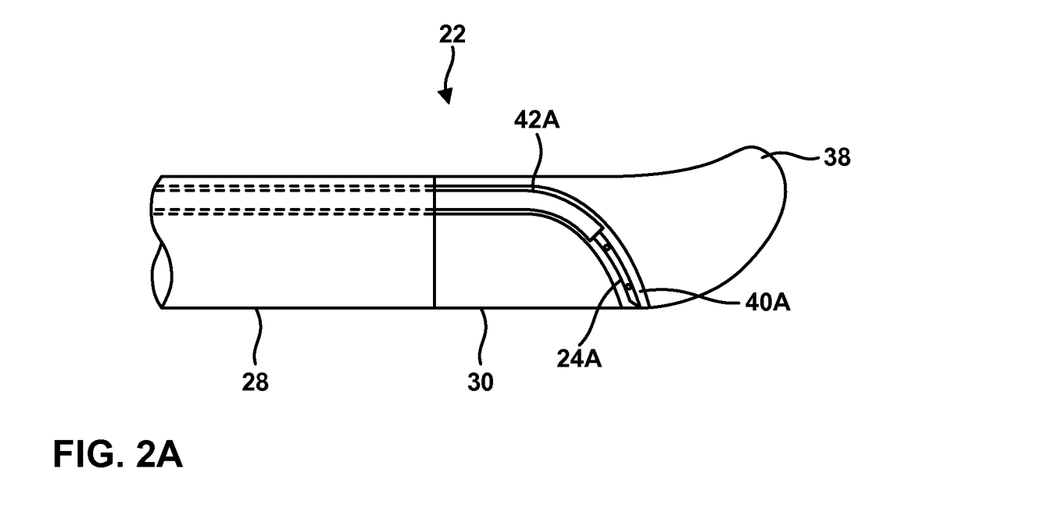
FIGS. 2A and 2B are cross-sectional side views of a distal end of a catheter of an ablation device.
Figure 2B:
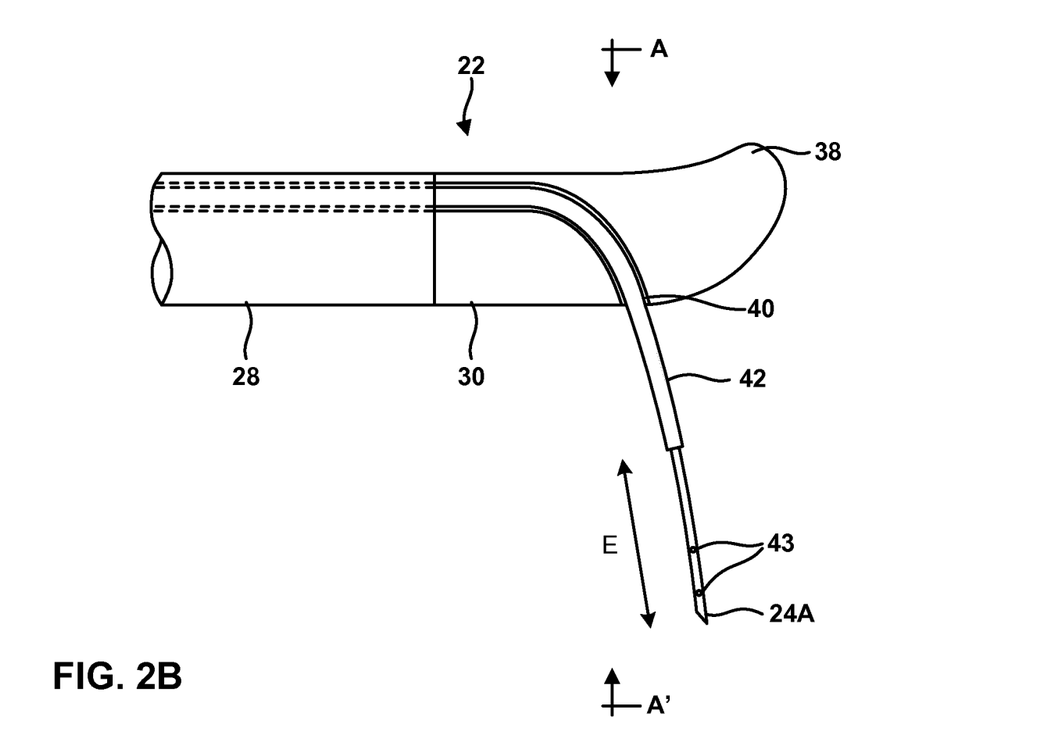

FIGS. 2A and 2B are cross-sectional side views of a distal end of a catheter, such as catheter 22 of ablation device 16 of FIG. 1. As shown in FIG. 2A, shaft 28 is coupled to tip 30 at the distal end of catheter 22. Tip 30 includes protrusion 38 that aids the insertion of catheter 22 through the urethra or other orifice of patient 12.

Catheter 22 includes a channel 40A that houses needle electrode 24A and allows needle electrode 24A to exit tip 30. Channel 40A extends from tip 30 through shaft 28 into the housing of ablation device 16 (FIG. 1). The curved portion of channel 40A in tip 30 deflects needle electrode 24A such that needle electrode 24A penetrates target tissue location 14 from a side of catheter 22. The curvature of channel 40A may be altered to produce different entry angles of needle electrode 24A. Thus, needle electrode 24A may exit at or near the side of catheter 22, wherein the side is a lengthwise edge substantially facing the wall of target tissue location 14. In some embodiments, channel 40A may be configured such that needle electrode 24A exits from the distal end of catheter 22 instead of from the side of catheter 22.

Needle electrode 24A is insulated with sheath 42A, such that the exposed portion of needle electrode 24A may deliver energy to target tissue location 14. Needle electrode 24A is deployed from tip 30 of catheter 22. Needle electrode 24A may, for example, be deployed via the clinicians interaction with trigger 32 (FIG. 1) of ablation device 16. FIG. 2B illustrates the distal end of catheter 22 after needle electrode 24A has been deployed from tip 30. The exposed length E of needle electrode 24A is variable by controlling the position of sheath 42A. Exposed length E may be controlled by the clinician to be generally between 1 mm and 50 mm. Once needle electrode 24A is deployed, needle electrode 24A may be locked into place until the ablation therapy is completed.

Ablation system 10 delivers energy to target tissue location 14 via deployed needle electrode 24A as well as needle electrode 24B (not shown in FIGS. 2A and 2B). Needle electrode 24B resides behind needle electrode 24A and thus cannot be seen in FIGS. 2A and 2B. Needle electrode 24B may be substantially similar to needle electrode 24A. As described above, energy may be transferred between electrodes 24A and 24B due to the close proximity of electrodes 24A and 24B within target tissue location 14. The cross talk may result in erroneous impedance measurements. The impedance measurement techniques described in this disclosure, however, may reduce the effect the crosstalk has on the impedance measurements. Moreover, the impedance measurement techniques may allow for better control of the delivery parameters of the therapy, as described herein.

In some embodiments, needle electrode 24A does not deliver a conductive fluid to the target tissue. In this case, needle electrode 24A may be solid or hollow and act as a dry electrode. Delivering energy through needle electrode 24A without a conductive fluid may simplify the ablation procedure and reduce the cost of ablation therapy. Alternatively, needle electrode 24A may be a hollow needle which allows conductive fluid, e.g., saline, to flow from therapy delivery device 15 to target tissue location 14. To this end, needle electrode 24A may include multiple holes 43 which allow the conductive fluid to flow into target tissue location 14 and increase the effective are to which needle electrode 24A may deliver therapy. The conductive fluid may also more evenly distribute the RF energy to the tissue to create more uniform lesions.

Figure 3:
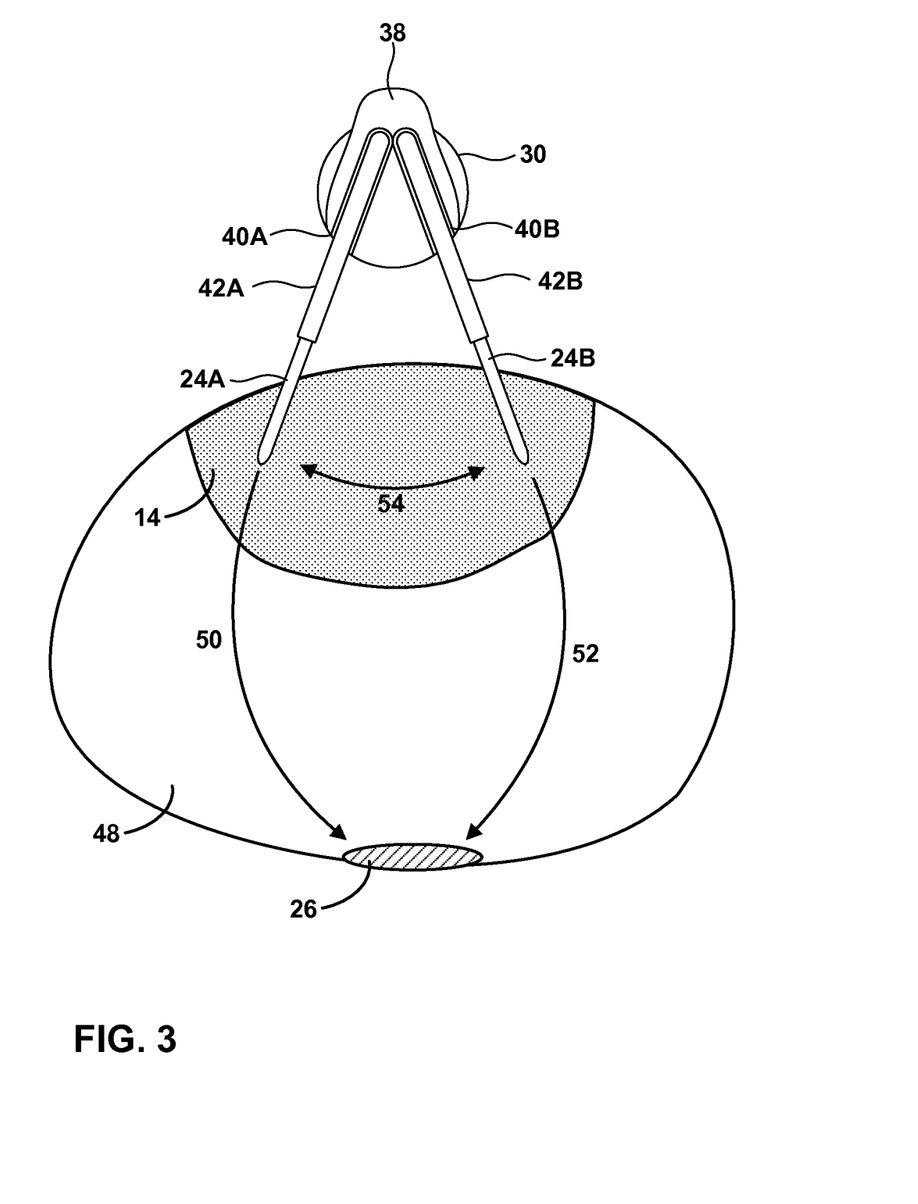
FIG. 3 is a cross-sectional front view of a distal end of a catheter in conjunction with a target tissue location.

FIG. 3 is a cross-sectional front view of an example a distal end of a catheter, such as catheter 22 of FIGS. 1 and 2, in conjunction with target tissue location 14. The example illustrated in FIG. 3 may, for example, be a cross-sectional front view of tip 30 of FIG. 2B taken from A to A'. As shown in FIG. 3, needle electrodes 24 are deployed from tip 30 of catheter 22 into target tissue location 14. Needle electrode 24A is housed within channel 40A and needle electrode 24B is housed within channel 40B. Channel 40B may mirror the path of channel 40A shown in FIGS. 2A and 2B. Channels 40A and 40B may or may not be identical in diameter.

In some embodiments, needle electrodes 24A and 24B are partially covered by sheathes 42A and 42B, respectively. As described above, the exposed length of needle electrodes 24 may be variable by controlling the position of sheaths 42. Additionally, sheaths 42 may prevent fluids from entering channels 40 when catheter 22 is used in a wet ablation system. Needle electrodes 24 may be constructed of similar materials or different materials. Exemplary materials may include stainless steel, nitinol, copper, silver, or an alloy including multiple metals. In any case, each of needle electrodes 24 may be flexible and conduct electricity to promote ablation therapy.

In the example illustrated in FIG. 3, needle electrodes 24 are deployed to the same extended length. Alternatively, needle electrodes 24 may be deployed to different extended lengths. The angle at which needle electrodes 24A and 24B exit tip 36 with respect to each other may be varied based on the procedure for which catheter 22 is being used. Generally, the angle between needle electrodes 24A and 24B is between 0 degrees and 120 degrees.

As described above, energy is delivered from generator 17 (FIG. 1) to target tissue location 14 via electrodes 24. The energy delivered to each of electrodes 24 flows through target tissue location 14 and body 48 of patient 12 to return electrode 26. Thus, return electrode 26 operates as a common destination for the energy delivered via electrodes 24. As illustrated in FIG. 3, return electrode 26 is placed on or near the opposing side of target tissue location 14. Arrow 50 illustrates the flow of a portion of the energy from electrode 24A to return electrode 26. Arrow 52 illustrates the flow of a portion of the energy from electrode 24A to return electrode 26. A substantial portion of the energy delivered to target tissue location 14 via electrodes 24 follow the path of arrows 50 and 52. However, since electrodes 24 are located in such close proximity to one another when disposed in target tissue location 14, some energy, e.g., in the form of current, may travel from one of electrodes 24 to the other one of electrodes 24. In other words, the close proximity of electrodes 24 may result in crosstalk between electrodes 24. Arrow 54 illustrates the crosstalk between electrodes 24.

Ablation system 10 may measure impedances between electrodes 24A and return electrode 26 and between electrode 24B and return electrode 26 to monitor and control the ablation therapy. If, for example, the impedance between one of electrodes 24 and return electrode 26 rises to an undesirable level, ablation system 10 may adjust the amount of energy being delivered to the respective one of electrodes 24. As an example, if the impedance between electrode 24A and return electrode 26 exceeds a threshold, processor 18 (FIG. 1) or a user may reduce the amount of energy delivered by generator 17 to electrode 24A. Due to the crosstalk between electrodes 24, however, the impedance measurements between electrodes 24 and return electrode 26 may not be accurate. In fact, sometimes the crosstalk may result in erroneously high impedance measurements. In some cases the erroneously high impedance measurements result in inadvertent reductions in the amount of energy delivered to one or both of electrodes 24. To more accurately measure the impedance between electrodes 24 and the common return electrode 26, ablation system 10 models the electrical interaction among electrode 24A, electrode 24B, and common return electrode 26 using a star-configuration resistor model and computes impedance values based on the model.

Figure 4:
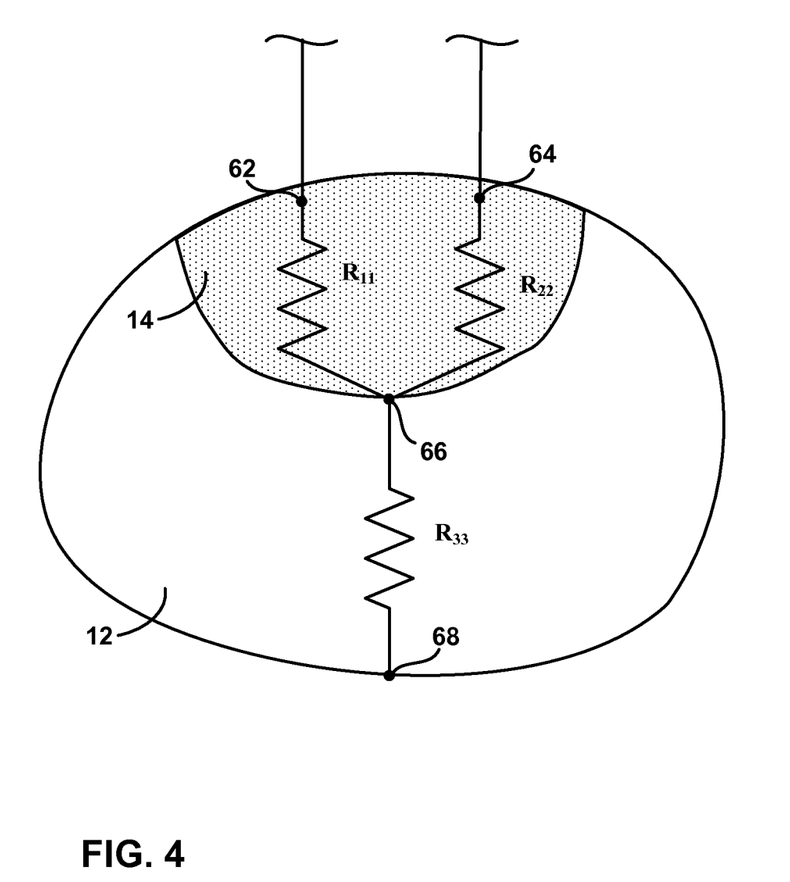
FIG. 4 is a circuit diagram illustrating an example star-configuration resistor model that models the interaction among a first and second active electrode and a return electrode.

FIG. 4 is a circuit diagram illustrating an example star-configuration resistor model that models the interaction among electrodes 24 and return electrode 26. In the example illustrated in FIG. 4, resistors $R_{11}$, $R_{22}$ and $R_{33}$ are coupled to form the star-configuration resistor model that models the electrical interaction among electrodes 24 and return electrode 26. The star-configuration resistor model is a model in which one terminal of each of resistors $R_{11}$, $R_{22}$ and $R_{33}$ is coupled at a central node 66. In particular, $R_{11}$ is an impedance on the leg of star network 60 from electrode 24A, $R_{22}$ is an impedance on the leg of star network 60 from electrode 24B, and $R_{33}$ is a common impedance to return electrode 26. In other words, $R_{11}$ is the impedance from node 62 to node 66, $R_{22}$ is the impedance from node 64 to node 66, and $R_{33}$ is the impedance from node 66 to node 68. Node 62 and 64 refer to the exposed portions of needle electrodes 24A and 24B, respectively, within target tissue location 14. Node 66 may represent a location just outside of a prostate of patient 12. Node 68 represents a point of contact between the body of patient 12 and return electrode 26, e.g., the small of the back in the case of treatment of a prostate condition.

Processor 18 uses model 60 to compute a more accurate approximation of the true impedance between each of electrodes 24 and return electrode 26. The basic electrical formulae for star resistor network model 60 are:

$$V_1 = I_1 * R_{11} + (I_1 + I_2) * R_{33} \tag{1}$$

$$V_2 = I_2 * R_{22} + (I_1 + I_2) * R_{33}, \tag{2}$$

where $V_1$ is a voltage on electrode 24A, $I_1$ is a current through electrode 24A, $V_2$ is a voltage on electrode 24B, and $I_2$ is a current through electrode 24B. Voltages $V_1$ and $V_2$ and currents $I_1$ and $I_2$ may, for example, be measured by one or more sensors within generator 17.

The true impedance between each of electrodes 24 and return electrode 26 is the impedance when the respective one of electrodes 24 is active. For example, the true impedance between electrode 24A and return electrode 26 is the impedance measured when electrode 24A is active and electrode 24B is inactive, i.e., no energy is transmitted via electrode 24B. Likewise, the true impedance between electrode 24B and return electrode 26 is the impedance measured when electrode 24B is active and electrode 24A is inactive. Thus, the true impedance is the impedance between the active one of electrodes 24 and return electrode 26 without any crosstalk. The true impedances between electrodes 24 and return electrode 26 can be defined as follows:

$$R_{13} = R_{11} + R_{33} \tag{3}$$

$$R_{23} = R_{22} + R_{33}, \tag{4}$$

where impedance $R_{13}$ is the electrical impedance between electrode 24A and return electrode 26 and impedance $R_{23}$ is the electrical impedance between electrode 24B and return electrode 26. In terms of the nodes of the circuit diagram, impedance $R_{13}$ is the electrical impedance between node 62 and node 68 and impedance $R_{23}$ is the electrical impedance between 64 and 68. In accordance with the techniques of this disclosure, processor 18 computes one or more parameters of the star configuration model and adjusts delivery of the therapy as a function of one of the computed parameters of the star-configuration resistor model. As described below, the computed parameters may comprise impedance values computed during a series of energy bursts.

When both electrodes 24A and 24B are active simultaneously, as is the case during delivery of ablation therapy, the measured impedances with the crosstalk are:

$$R_1 = V_1 / I_1 \tag{5}$$

$$R_2 = V_2 / I_2 \tag{6}$$

where $R_1$ is the measured impedance of electrode 24A and $R_2$ is the measured impedance of electrode 24B. As described above, voltages $V_1$ and $V_2$ and currents $I_1$ and $I_2$ may be measured by one or more sensors within generator 17, and may include crosstalk, e.g., in the form of current, from the other one of electrodes 24.

In one example, processor 18 may use the parameters, e.g., computed impedances, of the star-configuration model to compute a more accurate approximation of the true impedances ($R_{13}$ and $R_{23}$), i.e., the impedance values without the crosstalk. In other words, processor 18 computes a more accurate impedance measurement that accounts for the crosstalk between each of electrodes 24. Mathematical manipulation of formulae (1)-(4) provides the following equations for computing adjusted impedances between each of electrodes 24 and return electrode 26:

$$R_{13}=R_{11}+R_{33}=R_1-R_{33}*(I_2/I_1) \quad (7)$$

$$R_{23}=R_{22}+R_{33}=R_2-R_{33}*(I_1/I_2). \quad (8)$$

Therefore, it is possible to compute more accurate approximation of the true impedances ($R_{13}$ and $R_{23}$) during ablation therapy using the measured impedances of electrodes 24A and 24B (i.e., $R_1$ and $R_2$), electrical current measurements through electrode 24A and 24B (i.e., $I_1$ and $I_2$), and the common impedance to electrode 26 ($R_{33}$). The variables $R_1$, $R_2$, $I_1$ and $I_2$ may be measured during delivery of ablation therapy. In some embodiments, ablation system 10 includes one or more sensors that measure $R_1$, $R_2$, $I_1$ and $I_2$ during delivery of ablation therapy, i.e., while electrodes 24 are "active." In this manner, $R_1$, $R_2$, $I_1$ and $I_2$ are directly measured with hardware instrumentation within ablation system 10. In some embodiments, the impedance to common electrode 26 ($R_{33}$) may be computed prior to the beginning of the ablation therapy without deactivating one of electrodes 24. In some embodiments, processor 18 may temporarily interrupt delivery of the therapy to compute $R_{33}$. Alternatively, processor 18 of ablation system 10 may pre-compute the common impedance to electrode 26 (i.e., $R_{33}$) prior to initiation of the ablation therapy.

Processor 18 may compute $R_{33}$ using a series of energy bursts on different combinations of electrodes 24. Processor 18 may compute $R_{33}$ based on measurements, e.g., impedance measurements made during delivery of the series of energy bursts. Generator 17 delivers an energy burst to electrode 24A without delivering any energy to electrode 24B, i.e., a first combination of electrodes. During delivery this energy burst to only electrode 24A, ablation system 10 measures the impedance between electrode 24A and common return electrode 26 (i.e. $R_{13}$). Generator 17 also delivers an energy burst to electrode 24B without delivering any energy to electrode 24A, i.e., a second combination of electrodes. Again, ablation system 10 measures the impedance between electrode 24B and common return electrode 26 during delivery of the energy burst to only electrode 24B (i.e. $R_{23}$). Generator 17 delivers energy bursts of equal amplitude voltage, i.e., $V_1=V_2$ or $I_1*R_1=I_2*R_2$, to both electrode 24A and 24B concurrently, i.e., a third combination of electrodes, and measures the impedance of both electrodes 24A and 24B (i.e., $R_1$ and $R_2$). Processor 18 uses the impedance measurements made during the series of energy bursts to compute $R_{33}$ according to the equation:

$$R_{33}=((R_1-R_{13})/(R_1/R_2)+(R_2-R_{23})/(R_2/R_1))/2. \quad (9)$$

As described above, in some embodiments a physician, a clinician, a certified technician, or anyone trained to use ablation system 10 may, for example, deliver the initial energy bursts immediately prior to the beginning of the ablation therapy, i.e., before both RF electrodes are activated.

Processor 18 computes adjusted impedance measurements between each of electrodes 24 and common electrode 26 using impedances measured for electrodes 24A and 24B (i.e., $R_1$ and $R_2$), currents measured through electrodes 24A and 24 B (i.e., $I_1$ and $I_2$), and the computed common impedance to return electrode 26 ($R_{33}$). More specifically, processor 18 may compute the adjusted impedance measurements on-the-fly using the following equations:

$$R_{13}=R_1-R_{33}*(I_2/I_1) \quad (10)$$

$$R_{23}=R_2-R_{33}*(I_1/I_2). \quad (11)$$

In this manner, processor 18 may compute more accurate impedances between electrodes 24 and return electrode 26 ($R_{13}$ and $R_{23}$) on-the-fly, i.e., without disruption of the ablation therapy.

Processor 18 may use the adjusted impedance measurements to control delivery of the energy to target tissue location 14. In particular, when one of the impedance measurements exceeds a threshold limit, processor 18 may cause generator 17 to reduce the amount of energy delivered to the one of electrodes 24 corresponding to the high impedance measurement. Because the amount of energy delivered to each of electrodes 24 is controlled independently, generator 17 may continue to deliver the amount of energy initially being delivered to the other one of the electrodes 24, i.e., the electrode not associated with the high impedance measurement. In other words, only the energy delivered to one of the electrodes need be adjusted. Alternatively, processor 18 may display the impedance measurements to the user of ablation system 10, and the user may make manual adjustments to control the amount of energy delivered to electrodes 24 based at least in part on the impedance measurements.

In some embodiments, processor 18 may directly use the computed impedances of the star configuration model to adjust one or more parameters of the delivered therapy. For example, processor 18 may compute the common impedance to return electrode 26 ($R_{33}$) at two different instances of time and adjust the parameters of the therapy based on a comparison of the $R_{33}$ values at the different times. For example processor 18 may compute the common impedance to return electrode 26 prior to beginning therapy and then after beginning therapy, or at two different instances in time after beginning delivery of the therapy. Processor 18 may adjust the parameters of the therapy if the difference between the two computed common impedances exceeds a threshold. The user of ablation system 10 may adjust the location of electrodes 24 or remove electrodes 24 entirely and test them outside of the patient when the difference exceeds a threshold.

A similar determination may be made using impedances of the star configuration model prior to initiating therapy. For example, ablation system 10 may measure the impedance between electrode 24A and common return electrode 26 (i.e. $R_{13}$) during delivery an energy burst to electrode 24A without delivering any energy to electrode 24B. Ablation system 10 may also measures the impedance between electrode 24B and common return electrode 26 during delivery of an energy burst to electrode 24B without delivering any energy to electrode 24A. Processor 18 may then compare the measured impedances and adjust one or more parameters of the therapy when the difference between the first and second measured impedances exceeds a threshold. In this case, it is desirable that the energy burst applied to each of the electrodes 24 be of equal amplitude.

Figure 5:
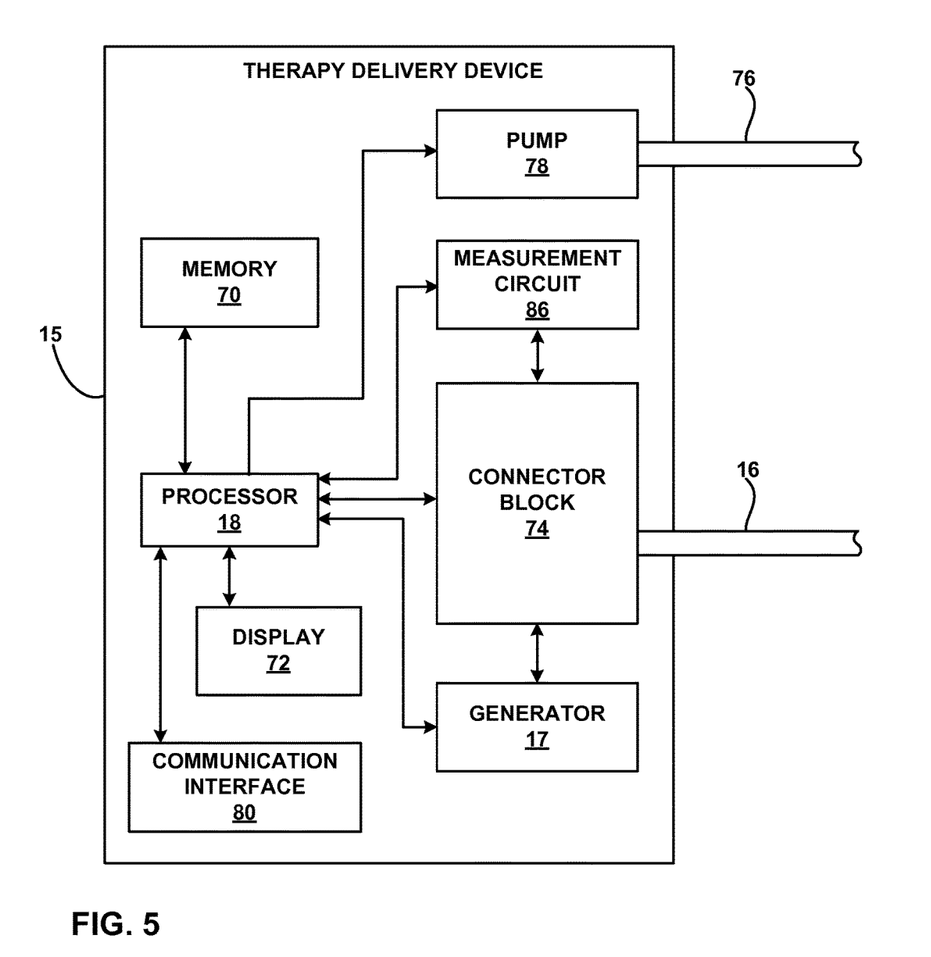
FIG. 5 is functional block diagram illustrating components of an exemplary therapy delivery device.

FIG. 5 is a functional block diagram illustrating components of an exemplary therapy delivery device, such as therapy delivery device 15 of FIG. 1. Therapy delivery device 15 includes a generator 17, a processor 18, a memory 70, a display 72, a connector block 74, a pump 78, a communication interface 80, and a measurement circuit 86. As shown in FIG. 5, connector block 74 is coupled to cable 16 for delivering energy produced by generator 17 and detecting tissue properties, e.g., impedance, with measurement circuit 86. Pump 78 produces pressure to deliver fluid through tube 76.

Processor 18 controls generator 17 to deliver energy therapy through connector block 74 according to therapy parameter values stored in memory 70. Processor 18 may receive such parameter values from display 72 or communication interface 80, and store the parameter values in memory 70. When signaled by the clinician to begin energy therapy (e.g., ablation therapy), which may be a signal from therapy device 16 conveyed through connector block 74, processor 18 computes the common impedance to return electrode 26 (FIG. 1) via a series of energy bursts delivered by generator 17 through connector block 74 to different combinations of electrodes 24 (FIG. 1) in accordance with the techniques described herein. After pre-computing the common impedance to return electrode 26, processor 18 communicates with generator 17 to produce the appropriate energy. As described above, generator 17 may deliver energy to each of electrodes 24 (FIG. 1) independently. In other words, generator 17 may independently control the amount of energy delivered to each of electrodes 24, thus permitting delivery of different amounts of energy to each of electrodes 24.

Measurement circuit 86 may be configured to measure one or more electrical operating parameters of ablation delivery device 16. For example, measurement circuit 86 may measure impedances between electrodes 24 and return electrode 26, a voltage on one or both of electrodes 24, a current through one or both of electrodes 24, or the like. Processor 18 computes adjusted impedances between electrodes 24 and return electrode 26 using the measured operating parameters and the pre-computed common impedance to return electrode 26. For example, processor may compute the adjusted impedances in accordance with equations (10) and (11).

Processor 18 monitors the computed impedances and may make modifications to the energy delivery or fluid delivery based upon the measured tissue property. Processor 18 may, for example, compare the computed impedances to a threshold set by the clinician or a predetermined program. In response to identifying an impedance between one of electrodes 24 and return electrode 26 that exceeds the threshold, processor 18 may cause generator 17 to increase or decrease the amount of energy delivered to the respective one of electrodes 24.

In some embodiments, processor may additionally communicate with pump 78 to provide fluid, as needed, to irrigate the ablation site or provide fluid to the electrodes during wet electrode ablation. Processor 18 may increase or decrease the amount of fluid delivered via pump 78 based on the computed impedances. Modifying the energy or fluid delivery may be done individually or simultaneously.

Alternatively, processor 18 may display the computed impedances to a user of ablation system 10 via display 72. The user may then manually monitor and adjust the ablation therapy delivered to patient 12. Additionally, processor may detect high impedance measurements and issue an alert (either audible or visual) to the user via display 72.

Connector block 74 may contain an interface for a plurality of connections, not just the connection for cable 16. These other connections may include one for a return electrode or for separate tissue property sensors. As mentioned previously, connector block 74 may be a variety of blocks used to diagnose or treat a variety of diseases. All connector blocks may be exchanged and connect to processor 18 for proper operation.

Processor 18 may also control data flow from the therapy. Data such as RF energy produced, tissue properties measured from measurement circuit 86, and fluid flow may be channeled into memory 70 for analysis. Processor 18 may comprise any one or more of a microprocessor, DSP, ASIC, FPGA, or other digital logic circuitry. Memory 70 may include multiple memories for storing a variety of data. For example, one memory may contain therapy parameters, one may contain generator operational files, and one may contain measured therapy data. Memory 70 may include any one or more of a random access memory (RAM), read-only memory (ROM), electronically-erasable programmable ROM (EEPROM), flash memory, or the like.

Figure 6:
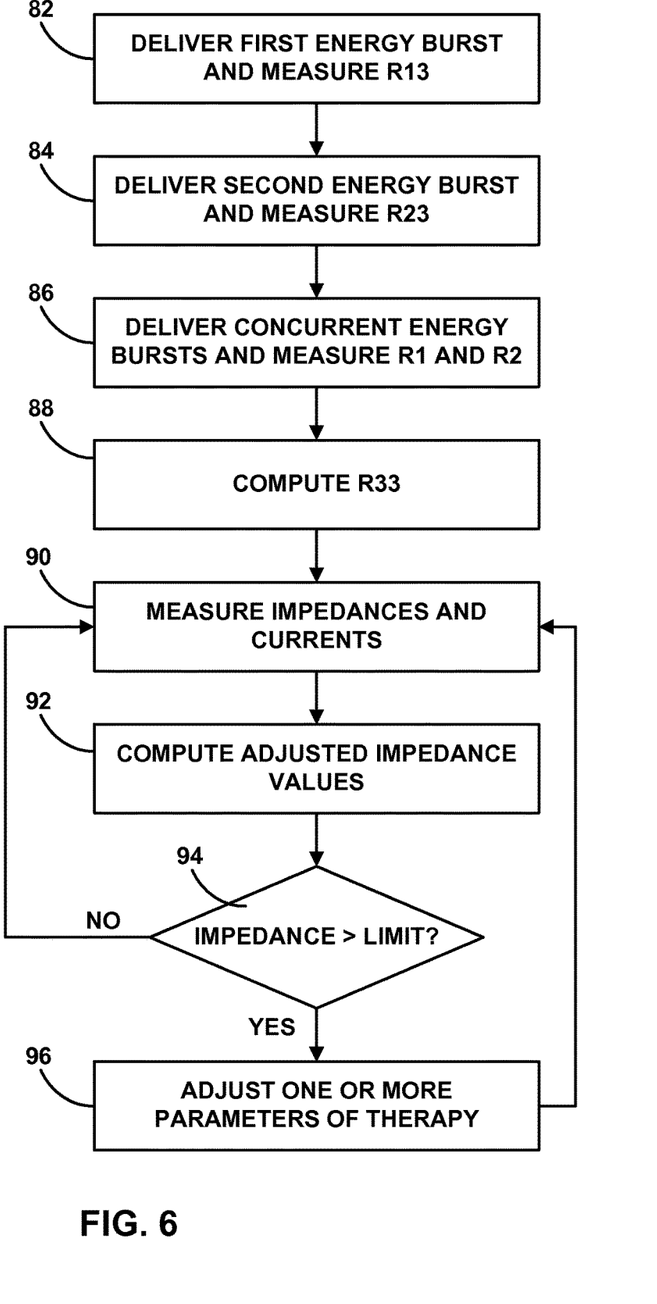
FIG. 6 is a flow diagram illustrating exemplary operation of an ablation system computing more accurate impedance measurements and controlling therapy based on the impedance measurements in accordance with the techniques of this disclosure.

FIG. 6 is a flow diagram illustrating exemplary operation of ablation system 10 computing more accurate impedance measurements and controlling therapy based on the impedance measurements in accordance with the one of the techniques of this disclosure. Ablation system 10 delivers an energy burst on electrode 24A (FIG. 1) and measures the impedance between electrode 24A and common return electrode 26, i.e., $R_{13}$ (82). The energy is delivered to electrode 24A without any energy being delivered to electrode 24B. Ablation system 10 also delivers an energy burst on electrode 24B and measures the impedance between electrode 24B and return electrode 26, i.e., $R_{23}$ (84). The energy is delivered to electrode 24B without any energy being delivered to electrode 24A. Additionally, ablation system 10 delivers energy of equal amplitude voltage on both electrode 24A and 24B, and measures impedance on both electrodes 24A and 24B ($R_1$ and $R_2$) (86). $R_1$ and $R_2$ may, for example, be computed using equation (5) and (6) above, in which some of the variables will be known and others may be measured. For example, $V_1$ and $V_2$ may be known and $I_1$ and $I_2$ may be measured upon delivery of the energy to electrodes 24. Processor 18 computes a common impedance to return electrode 26 (i.e., $R_{33}$) using the variables measured during the series of energy pulses (88). In particular, processor 18 may compute $R_{33}$ using equation (9) above. The series of energy pulses described above may be delivered in any order to obtain the variables for computing $R_{33}$. Moreover, the series of energy bursts may be delivered prior to initiation of the therapy or after beginning the therapy. In the latter case, the therapy may be temporarily disrupted.

During delivery of the ablation therapy, ablation system 10 measures impedance values between each of electrodes 24 and the return electrode 26 as well as current levels through each of electrodes 24 (90). Based on these measurements, processor 18 computes more accurate impedance measurements between each of electrodes 24 and return electrode 26 to account for cross talk between electrodes 24 (92). Processor 18 may, for example, compute the adjusted impedance values in accordance with equations (10) and (11). Moreover, processor 18 may compute these more accurate impedance values without disabling one of the electrodes 24 and disrupting the ablation therapy.

Processor 18 determines whether either of the adjusted impedance values exceeds a threshold impedance limit (94). If neither of the adjusted impedance values exceeds the threshold limit, ablation device continues to periodically measure impedances and currents and compute adjusted impedance values. If either of the adjusted impedance values does exceed the threshold limit, however, generator 17 adjusts one or more parameters of the delivered therapy (96). In one example, processor 18 may cause generator 17 to reduce the amount of energy delivered to the one of electrodes 24 corresponding to the high impedance measurement. Alternatively, processor 18 may display the impedance measurements to the user of ablation system 10, and the user may make manual adjustments based at least in part on the impedance measurements.

Figure 7:
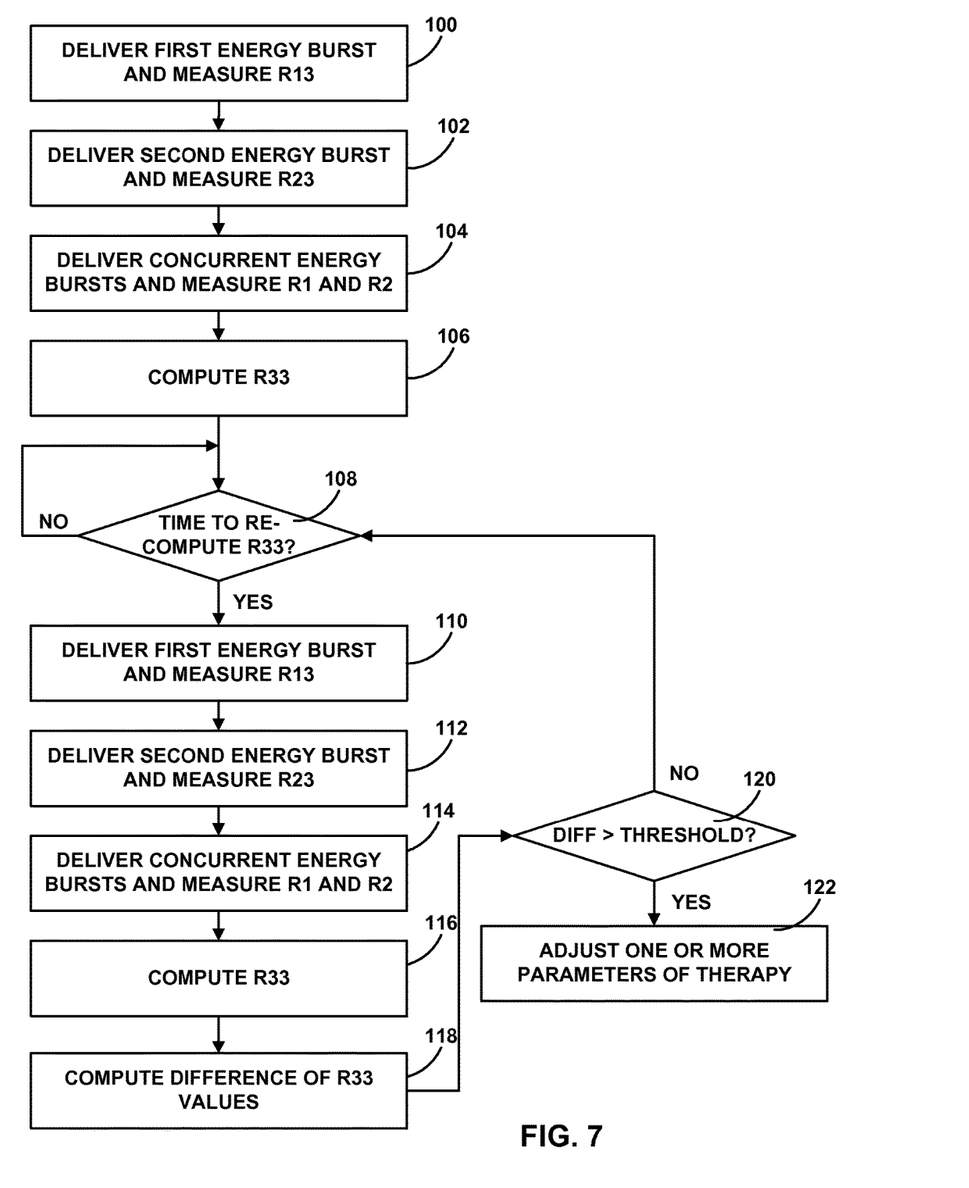
FIG. 7 is a flow diagram illustrating exemplary operation of an ablation system adjusting one or more parameters of the delivered therapy based on a comparison of the common impedance measured at two different instances in time.

FIG. 7 is a flow diagram illustrating exemplary operation of ablation system 10 adjusting one or more parameters of the delivered therapy based on one or more impedances computed for the star-configuration model. Ablation system 10 delivers an energy burst on electrode 24A (FIG. 1) and measures the impedance between electrode 24A and common return electrode 26, i.e., $R_{13}$ (100). The energy is delivered to electrode 24A without any energy being delivered to electrode 24B. Ablation system 10 also delivers an energy burst to electrode 24B and measures the impedance between electrode 24B and return electrode 26, i.e., $R_{23}$ (102). The energy is delivered to electrode 24B without any energy being delivered to electrode 24A. Additionally, ablation system 10 delivers energy of equal amplitude voltage on both electrode 24A and 24B, and measures impedance on both electrodes 24A and 24B ($R_1$ and $R_2$) (104). $R_1$ and $R_2$ may, for example, be computed using equation (5) and (6) above, in which some of the variables will be known and others may be measured. For example, $V_1$ and $V_2$ may be known and $I_1$ and $I_2$ may be measured upon delivery of the energy to electrodes 24. Processor 18 computes a common impedance to return electrode 26 (i.e., $R_{33}$) using the variables measured during the series of energy pulses (106). In particular, processor 18 may compute $R_{33}$ using equation (9) above. The series of energy pulses described above may be delivered in any order to obtain the variables for computing $R_{33}$. Moreover, the series of energy bursts may be delivered prior to initiation of the therapy or after beginning the therapy. In the latter case, the therapy may be temporarily disrupted.

Processor 18 determines whether it is time to re-compute $R_{33}$ (108). Processor may periodically compute $R_{33}$ to ensure proper operation of electrodes 24. When processor 18 determines that it is time to re-compute $R_{33}$, ablation system 10 delivers another energy burst on electrode 24A (FIG. 1) and measures the impedance between electrode 24A and common return electrode 26, i.e., $R_{13}$ (110). The energy is again delivered to electrode 24A without any energy being delivered to electrode 24B. Ablation system 10 also delivers another energy burst on electrode 24B and measures the impedance between electrode 24B and return electrode 26, i.e., $R_{23}$ (112). The energy is again delivered to electrode 24B without any energy being delivered to electrode 24A. Additionally, ablation system 10 delivers energy of equal amplitude voltage on both electrode 24A and 24B, and measures impedance on both electrodes 24A and 24B ($R_1$ and $R_2$) (114). $R_1$ and $R_2$ may, for example, be computed using equation (5) and (6) above, in which some of the variables will be known and others may be measured. For example, $V_1$ and $V_2$ may be known and $I_1$ and $I_2$ may be measured upon delivery of the energy to electrodes 24. Processor 18 computes a common impedance to return electrode 26 (i.e., $R_{33}$) using the variables measured during the series of energy pulses (116). In particular, processor 18 may compute $R_{33}$ using equation (9) above.

Processor 18 computes a difference between the first computed $R_{33}$ and the second computed $R_{33}$ value (118). Processor 18 determines whether the difference exceeds a threshold difference (120). If the difference does not exceed the threshold difference, processor 18 waits until it is time to re-compute $R_{33}$ again. If the difference does exceed the threshold difference, processor 18 adjusts one or more parameters of the delivered therapy (122). Processor 18 may, for example, cause generator 17 to reduce the amount of energy delivered to the one of electrodes 24, relocated the electrodes, test operation of the electrodes to determine if one is broke, or the like.

Figure 8:
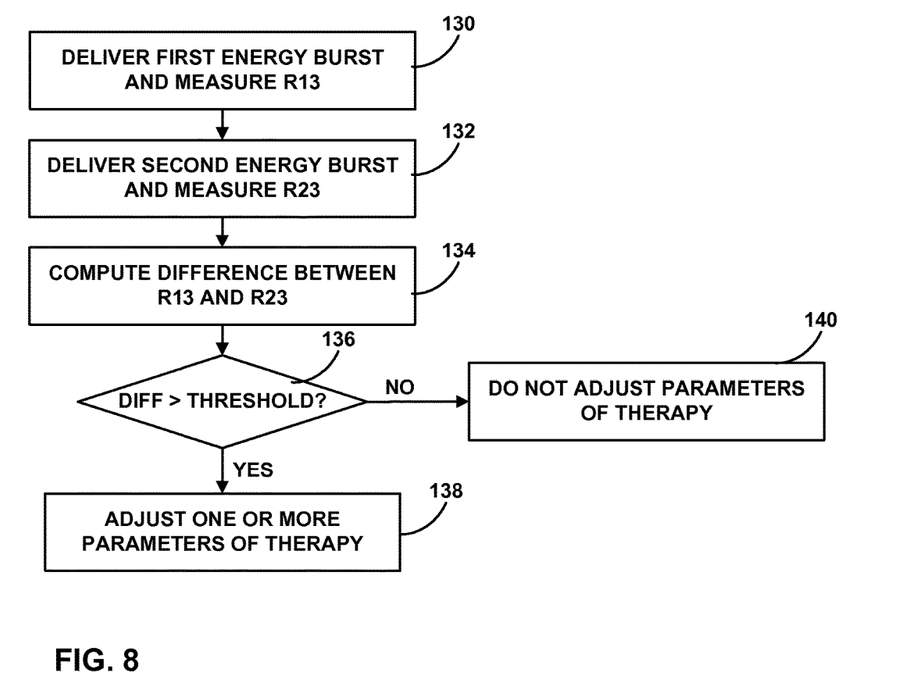
FIG. 8 is a flow diagram illustrating exemplary operation of an ablation system adjusting one or more parameters of the delivered therapy based on a comparison of the true impedances between the electrodes and a return electrode.

FIG. 8 is a flow diagram illustrating exemplary operation of ablation system 10 adjusting one or more parameters of the delivered therapy based on one or more impedances computed for the star-configuration model. Ablation system 10 delivers an energy burst on electrode 24A (FIG. 1) and measures the impedance between electrode 24A and common return electrode 26, i.e., $R_{13}$ (130). The energy is delivered to electrode 24A without any energy being delivered to electrode 24B. Ablation system 10 also delivers an energy burst on electrode 24B and measures the impedance between electrode 24B and return electrode 26, i.e., $R_{23}$ (132). The energy is delivered to electrode 24B without any energy being delivered to electrode 24A.

Processor 18 computes a difference between $R_{13}$ and $R_{23}$ (134). Processor 18 determines whether the difference exceeds a threshold difference (136). If the difference exceeds the threshold difference, processor 18 adjusts one or more parameters of the delivered therapy (138). Processor 18 may, for example, cause generator 17 to reduce the amount of energy delivered to the one of electrodes 24, relocated the electrodes, test operation of the electrodes to determine if one is broke, or the like. If the difference does not exceed the threshold difference, processor 18 does not adjust any parameters of the therapy (140).

Various embodiments of have been the described in this disclosure. These embodiments may include processors that are realized by one or more microprocessors, ASICs, FPGAs, or other equivalent integrated logic circuitry. In some embodiments, a computer-readable medium may store instructions that cause a processor to perform the techniques described herein. The processor may utilize several different types of storage methods to store the computer-readable instructions for the device operation and data storage. These memory and storage media types may include a type of hard disk, RAM, or flash memory, e.g. CompactFlash or SmartMedia.

The preceding specific embodiments are illustrative of the practice of the techniques of this disclosure. It is to be understood, therefore, that other expedients known to those skilled in the art or disclosed herein may be employed without departing from the scope of the following claims.

The invention claimed is:

1. An ablation system for delivering therapy to treat a condition of a human patient, the ablation system comprising:
   a catheter configured for insertion through a urethra or other orifice to a site within the patient, wherein the catheter comprises first and second electrodes adapted for delivering energy to tissue;
   a return electrode positionable interiorly or exteriorly of the patient to operate as a destination for the energy delivered via the first and second electrodes; and
   a therapy delivery device coupled to the catheter, the therapy delivery device including:
      a generator configured to deliver energy to the tissue of a target tissue location of the patient via the first electrode, the second electrode, and the return electrode; and
      a processor having instructions configured for (a) computing one or more parameters of an electrical interaction between the first and second electrodes and the return electrode using a star-configuration resistor model in which all resistors of the star-configuration resistor model are coupled to each other at a common node and (b) adjusting, based on at least one of the one or more computed parameters of the star-configuration resistor model, one or more parameters of the delivered therapy, wherein the one or more computed parameter of the star-configuration resistor model comprises a common impedance to the return electrode of the star-configuration resistor model.

2. The ablation system of claim 1, wherein the generator is configured to independently control an amount of energy delivered to the first electrode and the second electrode.

3. The ablation system of claim 1, wherein the one or more computed parameters comprise one or more measured voltages, measured currents, or computed impedances.

4. The ablation system of claim 1, wherein the generator is configured to independently control an amount of energy delivered to the first electrode and the second electrode, and wherein the processor comprises instructions configured for computing the one or more parameters of the star-configuration resistor model prior to beginning delivery of the delivered therapy to the patient.

5. The ablation system of claim 1, wherein the generator is configured to independently control an amount of energy delivered to the first electrode and the second electrode, and wherein the processor comprises instructions configured for computing the one or more parameters of the star-configuration resistor model after beginning delivery of the delivered therapy to the patient.

6. The ablation system of claim 1, wherein the first electrode comprises a first needle electrode and the second electrode comprises a second needle electrode.

7. The ablation system of claim 1, wherein the first electrode comprises a first ring electrode and the second electrode comprises a second ring electrode.

8. The ablation system of claim 1, wherein the catheter comprises:
   a shaft permanently coupled to a housing of the catheter; and
   a tip coupled to the shaft.

9. The ablation system of claim 8, wherein the shaft is adapted to be replaced and discarded after a single use of the catheter.

10. The ablation system of claim 8, wherein the tip comprises openings positioned to allow extension of the first and second electrodes from the catheter toward the target tissue location.

11. An ablation system for delivering therapy to treat a condition of a human patient, the ablation system comprising:
   a first electrode and a second electrode both configured to deliver energy to tissue;
   means for inserting, through a urethra or other orifice, the first electrode and the second electrode to a site within the patient;
   a return electrode positionable interiorly or exteriorly of the patient to operate as a destination for the energy delivered via the first and second electrodes;
   means for delivering the energy to the tissue of a target tissue location of the patient via the first electrode, the second electrode, and the return electrode; and
   means for:
      computing one or more parameters of an electrical interaction between the first and second electrodes and the return electrode using a star-configuration resistor model in which all resistors of the star-configuration resistor model are coupled to each other at a common node, wherein the one or more computed parameters of the star-configuration resistor model comprises a common impedance to the return electrode of the star-configuration resistor model; and
      adjusting, based on at least one of the one or more computed parameters of the star-configuration resistor model, one or more parameters of the delivered therapy.

* * * * *